US00PP21452P2

(12) United States Plant Patent
Pan

(10) Patent No.: US PP21,452 P2
(45) Date of Patent: Nov. 9, 2010

(54) ***LANTANA* PLANT NAMED 'BANI REDDA'**
(50) Latin Name: *Lantana camara L.*
Varietal Denomination: Bani Redda

(75) Inventor: Shifeng Pan, Hollister, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/589,146

(22) Filed: Oct. 19, 2009

(51) Int. Cl.
*A01H 5/00* (2006.01)

(52) U.S. Cl. ..... Plt./227
(58) Field of Classification Search ..... Plt./227
See application file for complete search history.

*Primary Examiner*—Annette H Para
(74) *Attorney, Agent, or Firm*—S. Matthew Edwards

(57) ABSTRACT

A new *Lantana* plant named 'Bani Redda,' particularly distinguished by the large bold yellow flowers that turn orange-red, excellent floriferousness because of limited seed set, compact and dense mounding habit with dark green foliage.

1 Drawing Sheet

Latin name of the genus and species of the plant claimed: *Lantana camara L.*

Varietal denomination: 'Bani Redda'.

BACKGROUND OF THE NEW PLANT

The present invention comprises a new *Lantana*, botanically known as *Lantana camara L.* and hereinafter referred to by the variety name 'Bani Redda'.

'Bani Redda' is a product of a planned breeding program. The new cultivar 'Bani Redda' has large bold yellow flowers that turn orange-red, excellent floriferousness because of limited seed set, compact and dense mounding habit with dark green foliage.

'Bani Redda' originates from a self pollination in a controlled breeding program in Gilroy, Calif. The pollination was made in June 2004 and the seed sown in February 2005. The female parent was an unpatented, proprietary plant identified as '122' with fuschia color. '122' has lighter red flowers, larger and lighter foliage and a more open plant habit than 'Bani Redda'.

'Bani Redda' was selected as one flowering plant within the progeny of the stated cross in June 2005 in a controlled environment in Gilroy, Calif.

The first act of asexual reproduction of 'Bani Redda' was accomplished when vegetative cuttings were propagated from the initial selection in the June 2005 in a controlled environment in Gilroy, Calif.

BRIEF SUMMARY OF INVENTION

Horticultural examination of plants grown from cuttings of the plant initiated in June 2005 in Gilroy, Calif., and continuing thereafter, has demonstrated that the combination of characteristics as herein disclosed for 'Bani Redda' are firmly fixed and are retained through successive generations of asexual reproduction.

'Bani Redda' has not been observed under all possible environmental conditions. The phenotype may vary significantly with variations in environment such as temperature, light intensity and day length.

A Plant Breeder's Right for this cultivar was applied for in Canada on Jan. 30, 2009. 'Bani Redda' has not been made publicly available more than one year prior to the filing of this application.

The following traits have been repeatedly observed and are determined to be basic characteristics of the new variety. The combination of these characteristics distinguishes this *Lantana* as a new and distinct variety.

BRIEF DESCRIPTION OF THE PHOTOGRAPHS

The accompanying photographic drawing shows typical flower and foliage characteristics of 'Bani Redda' with colors being as true as possible with an illustration of this type. The photographic drawing shows 3 flowering potted plants of the new variety growing in a 14 inch container, and a close up of the flowers. These plants were grown outdoors in Gilroy, Calif. The plants were about 20 weeks of age when the photo was taken in July 2009.

DETAILED BOTANICAL DESCRIPTION

The plant descriptions and measurements were taken in Gilroy, Calif. in April 2009 on plants that were growing in 4.5 inch pots in a trial setting. These plants were about 16-18 weeks of age and were grown with several early sprays of Paclobutrazol, a plant growth regular.

Color Chart used: Royal Horticultural Society Colour Chart (R.H.S.) 2001.

TABLE 1

DIFFERENCES BETWEEN THE NEW VARIETY 'BANI REDDA' AND A SIMILAR VARIETY

| | 'Bani Redda' | 'Rivrred' (U.S. Plant Pat. No. 17,106) |
|---|---|---|
| Flower count: | More | Fewer |
| Flower size: | Larger | Smaller |
| Branching habit: | Better/longer | Less/shorter |
| Vigor: | More | Less |

Plant:

*Form, growth and habit.*—Semi-woody, grown as an annual or perennial; compact and dense mounding habit and well branched.

*Plant height.*—15-18 cm.

*Plant height* (*inflorescence included*).—17-21 cm.

*Plant width.*—25-30 cm.

Foliage:
*Type.*—Opposite.
*Immature, leaf color, upper surface.*—Little darker than RHS 146A.
*Lower surface.*—Closest to RHS 137C.
*Mature, leaf color, upper surface.*—Darker than RHS 147A.
*Lower surface.*—Closest to RHS 147B.
*Length.*—5.5-6.2 cm.
*Width.*—3.7-3.9 cm.
*Shape.*—Ovate.
*Base shape.*—Attenuate.
*Apex shape.*—Acute.
*Margin.*—Serrate.
*Texture, upper surface.*—Hispid and glandular hairs.
*Lower surface.*—Hispid and glandular hairs.
*Color of veins, upper surface.*—RHS 146A basally, otherwise indistinct.
*Color of veins, lower surface.*—RHS 146A basally, otherwise indistinct.
*Petiole color.*—RHS 146A.
*Petiole length.*—1.5-2.0 cm.
*Petiole diameter.*—0.25 cm.
*Texture.*—Hispid and glandular hairs.

Stem:
*Quantity of main branches per plant.*—4-5.
*Quantity of leaves per branch.*—8-12.
*Color of stem.*—RHS 146B.
*Length of stem.*—15-17 cm.
*Diameter.*—0.3 cm.
*Length of internodes.*—0.5-2.5 cm.
*Texture.*—Hispid and glandular hairs.

Inflorescence:
*Type.*—Umbel like, flattened semi-sphere the florets are sessile on an ovate receptacle.
*Blooming habit.*—Flowers continuously from spring through fall.
*Number of flowers per inflorescence.*—13-18 open with 15-20 buds.
*Quantity of inflorescences per plant.*—16-25.
*Lastingness of individual blooms on the plant.*—About 4 weeks (depending on temperatures).
*Fragrance.*—Spicy.
*Umbel horizontal diameter.*—4.5 cm.
*Umbel vertical height.*—1.75-2.0 cm.
*Color of peduncle.*—RHS 146B.
*Length of peduncle.*—3.0-5.0 cm.
*Peduncle diameter.*—0.2 cm.
*Texture.*—Hispid and glandular hairs.

Corolla:
*Form.*—Salver-shaped to shallow cup-shaped and zygomorphic, with a relatively long tube at the base. Each floret subtended by single bract.
*Floret horizontal diameter.*—1.1 cm.
*Floret depth.*—1.7 cm.
*Immature, Color of petals, upper surface.*—RHS 9A ground color with spots of RHS 46B around the margin.
*Lower surface.*—RHS 10B with patches of RHS 46C.
*Mature, color of petals, upper surface.*—Between RHS N30A and RHS 34A ground color overlaid with RHS 28A in irregular patches; maturing to between RHS 45A and RHS 46B.
*Lower surface.*—RHS 39C with RHS 50B in various shades at the margins.
*Petal length.*—0.4-0.5 cm.
*Petal diameter.*—0.3-0.6 cm.
*Apex.*—Slightly mucronulate.
*Margin.*—Entire.
*Shape.*—Obovate.
*Degree of lobation.*—Moderate.
*Texture, upper surface.*—Papillose.
*Lower surface.*—Slightly hirsute basally.
*Corolla tube, color, outer surface.*—RHS 10C basally with RHS 53C to RHS 53D at the throat flare.
*Inner surface.*—RHS 11C.
*Corolla tube length.*—1.2 cm.
*Diameter (at opening).*—0.2 cm.
*Corolla tube texture, outer surface.*—Hirsute.
*Inner surface.*—Hirsute.

Bud (just before opening):
*Color.*—RHS 45B.
*Length.*—0.7-0.8 cm.
*Width (cm).*—0.4 at the apex.
*Shape.*—Tubular with a flared apex.

Bract:
*Color.*—RHS 146B.
*Length.*—0.6-0.7 cm.
*Diameter.*—0.15-0.2 cm.
*Apex shape.*—Acute.
*Texture, upper (inner) surface.*—Glandular hairs.
*Lower (outside) surface.*—Hirsute.

Calyx:
*Number of sepals.*—5, fused sepals forming a short tube around the base of each floret.
*Color of sepals.*—RHS 145A to RHS 145B.
*Length of sepals.*—0.25-0.45 cm.
*Width of sepals.*—0.25 cm.
*Sepal shape.*—Tube-shaped with 2 short lobes.
*Apex shape.*—Obtuse.
*Texture, outer surface.*—Hirsute; glandular hairs.
*Inner surface.*—Glabrous.

Reproductive organs:
*Pistil.*—1.
*Length.*—0.3-0.4 cm.
*Style color.*—RHS 2C.
*Style length.*—0.15 cm.
*Stigma color.*—RHS 1B to RHS 1C.
*Stamens.*—4.
*Color of filaments.*—RHS 1C.
*Length filaments.*—0.2 cm.
*Anther color.*—RHS 15A.
*Length of anthers.*—0.1-0.15 cm.
*Anther shape.*—Ovoid.
*Pollen amount.*—Sparse.
*Color of pollen.*—RHS 10A.
*Fertility/seed set.*—This hybrid sets very few seeds, and those seeds were not observed for characteristics.

Disease/pest resistance: Disease resistance or susceptibility has not been observed on this hybrid.

What is claimed is:

1. A new and distinct variety of *Lantana* plant named 'Bani Redda,' substantially as illustrated and described herein.

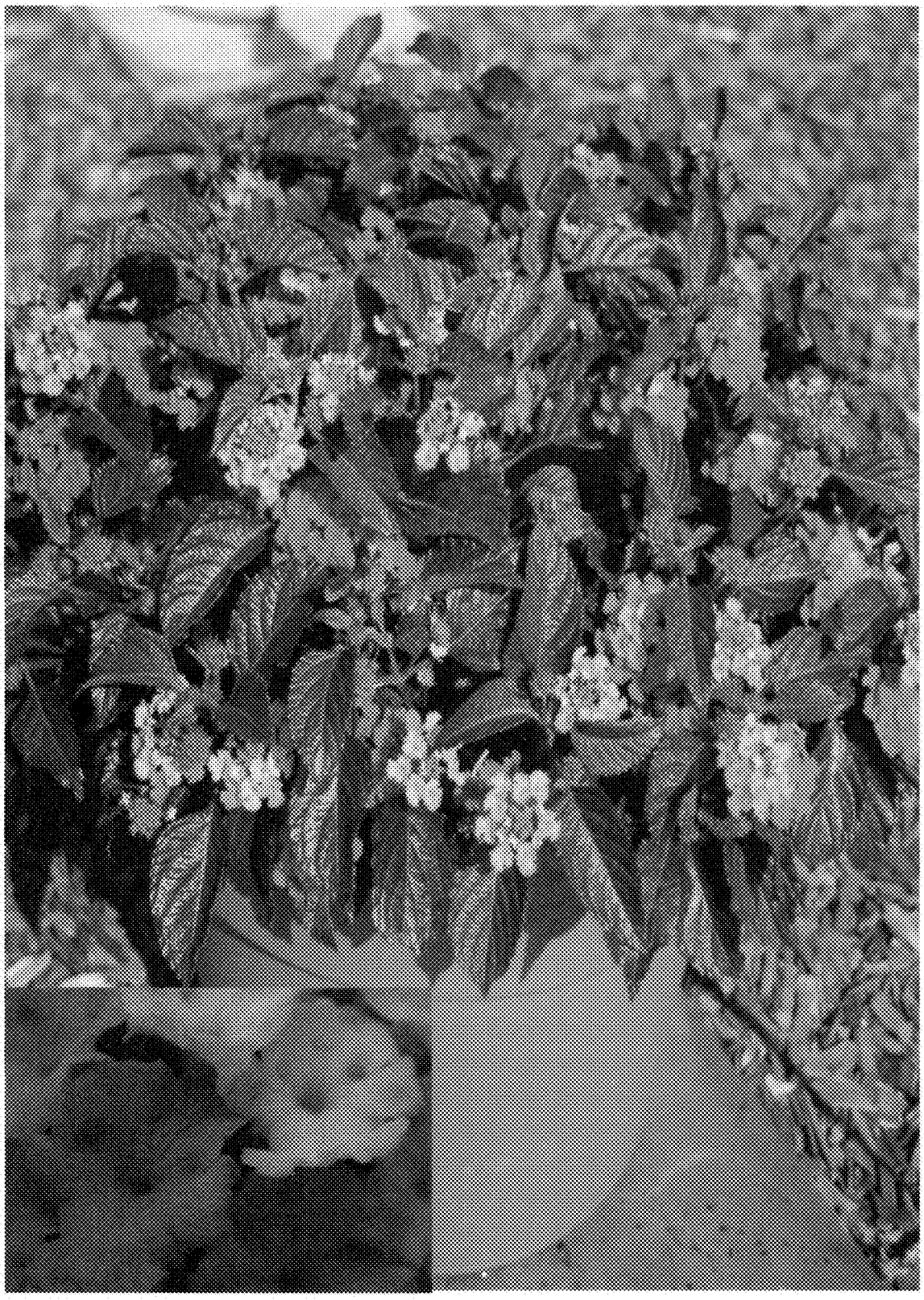

* * * * *